(12) United States Patent
Harrison et al.

(10) Patent No.: US 7,411,004 B2
(45) Date of Patent: Aug. 12, 2008

(54) SULPHONES WHICH MODULATE THE ACTION OF GAMMA SECRETASE

(75) Inventors: Timothy Harrison, Great Dunmow (GB); Paul Joseph Oakley, Bishop Stortford (GB); Martin Richard Teall, Bishop Stortford (GB)

(73) Assignee: Merck Sharp & Dohme Ltd., Hoddesdon, Hertfordshire (GB)

( * ) Notice: Subject to any disclaimer, the term of this patent is extended or adjusted under 35 U.S.C. 154(b) by 372 days.

(21) Appl. No.: 10/473,767

(22) PCT Filed: Aug. 21, 2001

(86) PCT No.: PCT/GB01/03778

§ 371 (c)(1),
(2), (4) Date: Oct. 1, 2003

(87) PCT Pub. No.: WO02/081433

PCT Pub. Date: Oct. 17, 2002

(65) Prior Publication Data

US 2004/0082617 A1    Apr. 29, 2004

(30) Foreign Application Priority Data

Apr. 5, 2001  (GB) ................................ 0108592.7

(51) Int. Cl.
*A61K 31/10*   (2006.01)
*C07C 317/14*  (2006.01)
(52) U.S. Cl. ......................................... 514/709; 568/34
(58) Field of Classification Search ................. 568/34; 514/709
See application file for complete search history.

(56) References Cited

U.S. PATENT DOCUMENTS 3,016,403 A * 1/1962 Dodson ..................... 568/32
4,379,921 A * 4/1983 Funaki et al. ............. 548/268.4
5,703,129 A    12/1997 Felsenstein et al.
6,013,649 A * 1/2000 Freskos et al. ............ 514/237.8

FOREIGN PATENT DOCUMENTS

| JP | 56-026847 |   | 3/1981 |
| JP | 8-53408 | * | 2/1996 |
| WO | WO 9803164 | * | 1/1998 |
| WO | WO 00/50391 |   | 8/2000 |
| WO | WO 03/055850 |   | 7/2003 |
| WO | WO 03/059335 |   | 7/2003 |

OTHER PUBLICATIONS

Database CAS Online on STN, Chem. Abstr., Accession No. 1908:3476, Posner, Contribution to our Knowledge of the Unsaturated Compounds. V. Addition of Mercaptans to Unsaturated Acids, Ber. (1908), 40, 4788-94, abstract only.*
Database CAS Online on STN, Chem. Abstr., Accession No. 1951: 41283, Balfe et al., Alkyll-oxygen fission in carboxylic esters. VII. Hydrolysis of methyl-2-naphthylcarbinyl hydrogen phthalate, Journal of the Chemical Society (1951) 380-1, abstract only.*
CAS Registry No. 329904-86-1 Indexed in STN Registry on Apr. 4, 2001.*
CAS Registry No. 95137-18-1 Indexed in STN Registry on Mar. 9, 1985.*
CAS Registry No. 94863-97-5 Indexed in STN Registry on Feb. 17, 1985.*
Jonczyk et al. Chemistry Letters, pp. 1557-1560, 1983.*
Marcantoni et al. Journal of Organic Chemistry (1998), 63(11), 3624-3630.*
Obushak et al., Russian Journal of General Chemistry (1997), 67(8), 1317.*
Fournier et al. European Journal of Medicinal Chemistry (1982), 17(1), 53-8.*
Julia et al., Bulletin de la Societe Chimique de France (1976), (3-4, Pt. 2), 513-18.*
Julie et al., Bulletin de la Societ Chimique de France (1976), (11-12, Pt. 2), 1941-6.*
Redman et al., Journal of the Chemical Societ, Perkin Transactions 2: Physical Organic Chemistry (1972-1999) (1978), (11), 1135-44.*
Pascali et al. Journal of the Chemical Society, Perkin Transactions 1: Organic and Bio-Organic Chemistry (197201999) (1973), (11), 1166-8.*
Yamamot et al. Bulletin of the Chemical Society of Japan (1987), 60(4), 1523-4.*
Marczak et al. Synthetic Communications (1990), 20(10), 1511-20.*
Messinger, P. Archiv der Pharmazie (1973), 306(6), 458-62.*
Chang et al. Journal of Organic Chemistry (1978), 43(2), 373-4.*
Vidal et al. Tetrahedron Letters (1986), 27(32), 3733-6.*
M. Makosza et al., "Ambiphilic Reactivity of 2,4-Dinitrobenzyl p-Tolyl Sulfone Carbanion", Polish. J. Chem., vol. 72, pp. 1198-1201 (1998).

* cited by examiner

*Primary Examiner*—Rebecca L Anderson
(74) *Attorney, Agent, or Firm*—William Krovatin; Raynard Yuro

(57) ABSTRACT

Disclosed are sulphones which modulate the action of gamma-secretase. The compounds are useful in the treatment or prevention of Alzheimer's disease.

1 Claim, No Drawings

SULPHONES WHICH MODULATE THE ACTION OF GAMMA SECRETASE

CROSS REFERENCE TO RELATED APPLICATIONS

This application is a U.S. National Phase application under 35 U.S.C. § 371 of PCT Application No. PCT/GB01/03778, filed Aug. 21, 2001, which claims priority under 35 U.S.C. § 119 from GB Application No. 0108592.7, filed Apr. 5, 2001.

The present invention relates to a novel class of compounds, their salts, pharmaceutical compositions comprising them, processes for making them and their use in therapy of the human body. In particular, the invention relates to novel sulphones which modulate the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ), and although the exact role of the plaques in the onset and progress of AD is not fully understood, it is generally accepted that suppressing or attenuating the secretion of Aβ is a likely means of alleviating or preventing the condition. (See, for example, ID *research alert* 1996 1(2):1-7; ID *research alert* 1997 2(1):1-8; Current Opinion in CPNS Investigational Drugs 1999 1(3):327-332; and Chemistry in Britain, Jan. 2000, 28-31.)

Aβ is a peptide comprising 39-43 amino acid residues, formed by proteolysis of the much larger amyloid precursor protein. The amyloid precursor protein (APP or AβPP) has a receptor-like structure with a large ectodomain, a membrane spanning region and a short cytoplasmic tail. Different isoforms of APP result from the alternative splicing of three exons in a single gene and have 695,751 and 770 amino acids respectively.

The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate the soluble, COOH-truncated forms of APP ($APP_s$). Proteases which release APP and its fragments from the membrane are termed "secretases". Most $APP_s$ is released by a putative α-secretase which cleaves within the Aβ domain (between residues $Lys^{16}$ and $Leu^{17}$) to release α-$APP_s$ and precludes the release of intact Aβ. A minor portion of $APP^s$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that β-secretase itself depends for its activity on the presence of presenilin-1. In a manner that is not fully understood presenilin-1 appears to undergo autocleavage.

There are relatively few reports in the literature of compounds with inhibitory activity towards β- or γ-secretase, as measured in cell-based assays. These are reviewed in the articles referenced above. Many of the relevant compounds are peptides or peptide derivatives.

The present invention provides a novel class of non-peptidic compounds which are useful in the treatment or prevention of AD by modulating the processing of APP by the putative γ-secretase, thus arresting the production of Aβ.

Japanese published Patent Application No. 56-26847 discloses certain 4-(4'-halophenyl)-4-phenylsulphonylbutyrate esters as reaction intermediates.

The present invention provides a pharmaceutical composition comprising, in a pharmaceutically acceptable carrier, a compound of formula I:

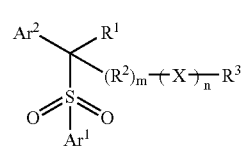

wherein:

$Ar^1$ represents $C_{6-10}$aryl or heteroaryl, either of which bears 0-3 substituents independently selected from halogen, CN, $NO_2$, $CF_3$, OH, $C_{1-4}$alkoxy or $C_{1-4}$alkyl which optionally bears a substituent selected from halogen, CN, $NO_2$, $CF_3$, OH and $C_{1-4}$alkoxy;

$Ar^2$ represents $C_{6-10}$aryl or heteroaryl, either of which bears 0-3 substituents independently selected from halogen, CN, $NO_2$, $CF_3$, OH, $C_{1-4}$alkoxy or $C_{1-4}$alkyl which optionally bears a substituent selected from halogen, CN, $NO_2$, $CF_3$, OH and $C_{1-4}$alkoxy;

$R^1$ represents H, or $C_{1-6}$allyl, $C_{3-6}$cycloalkyl or $C_{2-6}$alkenyl, any of which is optionally substituted by halogen, CN, $NO_2$, $CF_3$, OH, $C_{1-4}$alkoxy or $C_{1-4}$alkoxycarbonyl;

$R^2$ represents a saturated or unsaturated hydrocarbon linking group of up to 6 carbon atoms;

X represents —O—, —S—, —$SO_2$—, —N($R^4$)—, —C(O)—, —OC(O)—, —C(O)O—, —C(O)N($R^4$)—, —N($R^4$)C(O)—, —OC(O)O—, —N($R^4$)C(O)O—, —OC(O)N($R^4$)—, —$SO_2$N($R^4$)— or —N($R^4$)$SO_2$—;

$R^3$ represents $C_{1-10}$alkyl, $C_{3-9}$cycloalkyl, $C_{3-9}$cycloalkyl$C_{1-6}$alkyl, $C_{2-6}$alkenyl or $C_{2-6}$alkynyl, any of which may be substituted by halogen, CN, $NO_2$, $CF_3$, Ar, heterocyclyl, $OR^4$, $N(R^4)_2$, $COR^4$, $CO_2R^4$, $OCOR^4$, or $CON(R^4)_2$; or $R^3$ represents Ar or heterocyclyl;

$R^4$ represents H, $C_{1-4}$alkyl or Ar, or two $R^4$ groups together with a nitrogen atom to which they are mutually attached may complete an N-heterocyclyl group;

Ar represents phenyl or heteroaryl bearing 0-3 substituents selected from halogen, $C_{1-4}$alkyl, CN, $NO_2$, $CF_3$, OH, $C_{1-4}$alkoxy, $C_{1-4}$alkoxycarbonyl, amino, $C_{1-4}$alkylamino, di($C_{1-4}$alkyl)amino, carbamoyl, $C_{1-4}$alkylcarbamoyl and di($C_{1-4}$alkyl)carbamoyl;

m and n are each 0 or 1, provided that m=0 if n=0;

"heterocyclyl" at every occurrence thereof means a cyclic or polycyclic system of up to 10 ring atoms selected from C, N, O and S, wherein none of the constituent rings is aromatic and wherein at least one ring atom is other than C, bearing 0-3 substituents selected from =O, =S, halogen, $C_{1-4}$alkyl, CN, $NO_2$, $CF_3$, OH, $C_{1-4}$alkoxy, $C_{1-4}$alkoxycarbonyl, amino, $C_{1-4}$alkylamino, di($C_{1-4}$alkyl)amino, carbamoyl, Ar and COAr; and "heteroaryl" at every occurrence thereof means a cyclic or polycyclic system of up to 10 ring atoms selected from C, N, O and S, wherein at least one of the constituent rings is aromatic and wherein at least one ring atom of said aromatic ring is other than C;

or a pharmaceutically acceptable salt thereof.

The invention further provides a compound according to Formula I as defined above, or a pharmaceutically acceptable salt thereof, with the proviso that when m and n are both 1, $R^1$ is H, $R^2$ is —$CH_2CH_2$—, X is —C(O)O—, $R^3$ is methyl and $Ar^1$ is phenyl, $Ar^2$ is not 4-chlorophenyl or 4-fluorophenyl.

Where a variable occurs more than once in formula I or in a substituent thereof, the individual occurrences of that variable are independent of each other, unless otherwise specified.

As used herein, the expression "$C_{1-x}$alkyl" where x is an integer greater than 1 refers to straight-chained and branched alkyl groups wherein the number of constituent carbon atoms is in the range 1 to x. Particular alkyl groups include methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner.

The expression "$C_{3-9}$cycloalkyl" as used herein refers to nonaromatic monocyclic or fused bicyclic hydrocarbon ring systems comprising from 3 to 9 ring atoms. Examples include cyclopropyl, cyclobutyl, cyclopentyl, cyclohexyl, cyclohexenyl and bicyclo[2.2.1]heptyl.

The expression "$C_{3-6}$ cycloalkyl$C_{1-6}$alkyl" as used herein includes cyclopropylmethyl, cyclobutylmethyl, cyclopentylmethyl and cyclohexylmethyl.

The expression "$C_{6-10}$aryl" as used herein includes phenyl and naphthyl.

The expression "heterocyclyl" as used herein means a cyclic or polycyclic system of up to 10 ring atoms selected from C, N, O and S, wherein none of the constituent rings is aromatic and wherein at least one ring atom is other than carbon. Preferably not more than 3 ring atoms are other than carbon. Examples of heterocyclyl groups include azetidinyl, pyrrolidinyl, terahydrofuryl, piperidinyl, piperazinyl, morpholinyl, thiomorpholinyl, 2,5-diazabicyclo[2.2.1]heptyl, 2-aza-5-oxabicyclo[2.2.1]heptyl and 1,4-dioxa-8-azaspiro[4.5]decanyl. Unless otherwise indicated, heterocyclyl groups may be bonded through a ring carbon atom or a ring nitrogen atom where present. "C-heterocyclyl" indicates bonding through carbon, while "N-heterocyclyl" indicates bonding through nitrogen.

The expression "heteroaryl" as used herein means a cyclic or polycyclic system of up to 10 ring atoms selected from C, N, O and S, wherein at least one of the constituent rings is aromatic and wherein at least one ring atom is other than carbon. Preferably not more than 3 ring atoms are other than carbon. Where a heteroaryl ring comprises two or more atoms which are not carbon, not more than one of said atoms may be other than nitrogen. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of heteroaryl groups include 1,2,4-triazine and 1,3,5-triazine.

The term "halogen" as used herein includes fluorine, chlorine, bromine and iodine, of which fluorine and chlorine are preferred.

For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In formula I, $Ar^1$ represents $C_{6-10}$aryl or heteroaryl, either of which bears 0-3 substituents independently selected from halogen, CN, $NO_2$, $CF_3$, OH, $C_{1-4}$alkoxy or $C_{1-4}$alkyl which optionally bears a substituent selected from halogen, CN, $NO_2$, $CF_3$, OH and $C_{1-4}$alkoxy. Preferably, $Ar^1$ represents optionally substituted phenyl or heteroaryl. Typical heteroaryl embodiments of $Ar^1$ include optionally substituted pyridyl, in particular optionally substituted 3-pyridyl. Preferably, $Ar^1$ bears 0-2 substituents, more preferably 1 or 2 substituents, and most preferably 1 substituent which is preferably in the para-position relative to the sulphone group. Typical substituents include halogen (especially chlorine and fluorine), $C_{1-4}$alkoxy (such as methoxy), and $CF_3$. Examples of groups represented by $Ar^1$ include 4-chlorophenyl, 4-fluorophenyl, 4-trifluoromethylphenyl, 3,4-difluorophenyl, 3,4-dichlorophenyl, 4-methoxyphenyl and 6-chloro-3-pyridyl. Most preferably, $Ar^1$ represents 4-chlorophenyl.

$Ar^2$ represents $C_{6-10}$aryl or heteroaryl bearing 0-3 substituents independently selected from halogen, CN, $NO_2$, $CF_3$, OH, $C_{1-4}$alkoxy or $C_{1-4}$alkyl which optionally bears a substituent selected from halogen, CN, $NO_2$, $CF_3$, OH and $C_{1-4}$alkoxy. Preferably, $Ar^2$ represents phenyl bearing 1 or 2 substituents as indicated, and most preferably, $Ar^2$ represents 2,5-disubstituted phenyl. Preferred substituents include halogen (especially chlorine and fluorine) and substituted alkyl, such as hydroxymethyl. Examples of groups represented by $Ar^2$ include 2,5-dichlorophenyl, 2,5-difluorophenyl and 2-hydroxymethyl-5-fluorophenyl. Very aptly, $Ar^2$ represents 2,5-difluorophenyl.

$R^1$ represents H, or $C_{1-6}$alkyl, $C_{3-6}$cycloalkyl or $C_{2-6}$alkenyl, any of which is optionally substituted by halogen, CN, $NO_2$, $CF_3$, OH, $C_{1-4}$alkoxy or $C_{1-4}$alkoxycarbonyl. Typically, $R^1$ represents H, unsubstituted alkyl (such as methyl, ethyl, n-propyl or isopropyl), $C_{3-6}$cycloalkyl (such as cyclopropyl) or unsubstituted alkenyl (such as allyl). Preferably, $R^1$ represents H, methyl or allyl; most preferably $R^1$ represents H.

$R^2$ represents a saturated or unsaturated hydrocarbon linking group of up to 6 carbon atoms. Thus, $R^2$ is a bivalent group containing carbon and hydrogen atoms only, up to a maximum of 6 carbon atoms, but within those constraints may comprise any combination of linear, branched and cyclic structures, optionally comprising one or more double and/or triple bonds. Typically, $R^2$ (if present) represents a linear or branched alkylene group such as $CH_2$, $CH_2CH_2$, $CH_2CH_2CH_2$ or $CH(Me)CH_2$.

X represents a linking group selected from —O—, —S—, —$SO_2$—, —$N(R^4)$—, —C(O)—, —OC(O)—, —C(O)O—, —C(O)N(R⁴)—, —N(R⁴)C(O)—, —OC(O)O—, —N(R⁴)C(O)O—, —OC(O)N(R⁴)—, —SO₂N(R⁴)— and —N(R⁴)SO₂—, where R⁴ is as defined previously. In this context, R⁴ is preferably H. Typically, X represents an ether linkage —O—, an ester linkage —OC(O)— or —C(O)O—, an amide linkage —C(O)NH— or —NHC(O)—, or a carbamate linkage —NHC(O)O— or —OC(O)NH—. Preferably, X (if present) represents —C(O)O— or —OC(O)NH—.

m and n are individually 0 or 1 with the proviso that m must be 0 if n is 0. Thus, R² cannot be present unless X is also present, but X may be present regardless of whether R² is present.

R³ represents $C_{1-10}$alkyl, $C_{3-9}$cycloalkyl, $C_{3-9}$cycloalkyl$C_{1-6}$alkyl, $C_{2-6}$alkenyl or $C_{2-6}$alkynyl, any of which may be substituted by halogen, CN, NO₂, CF₃, Ar, heterocyclyl, OR⁴, N(R⁴)₂, COR⁴, CO₂R⁴, OCOR⁴, or CON(R⁴)₂; or R³ represents Ar or heterocyclyl. Typically, R³ represents $C_{1-6}$alkyl such as methyl, ethyl, n-propyl, isopropyl and t-butyl; $C_{3-6}$cycloalkyl such as cyclopropyl, cyclobutyl, cyclopentyl and cyclohexyl; $C_{3-6}$cycloalkyl$C_{1-6}$alkyl such as cyclobutylmethyl and cyclopropylmethyl; $C_{2-6}$alkenyl such as allyl, homoallyl and pent-1-en-5-yl; or $C_{1-6}$alkyl which is substituted with Ar, OR⁴, N(R⁴)₂ or CO₂R⁴, such as 1-phenylethyl, pyridylmethyl, 3-(imidazol-1-yl)propyl, 1-methyl-3-(morpholin-4-yl)propyl, 3-hydroxypropyl and 3-carboxypropan-2-yl.

In a first subclass of the compounds according to formula I, m and n are both 0. Within this subclass, R³ preferably represents $C_{1-6}$alkyl, $C_{3-6}$cycloalkyl, $C_{3-6}$cycloalkyl$C_{1-6}$alkyl or $C_{2-6}$alkenyl, any of which is optionally substituted with Ar, OR⁴, N(R⁴)₂ or CO₂R⁴.

In a second subclass of the compounds according to formula I, m and n are both 1. Within this subclass, R² is preferably a linear or branched alkylene group, X is preferably an ester, amide or carbamate linkage, and R³ preferably represents $C_{1-6}$alkyl, $C_{3-6}$cycloalkyl, $C_{3-6}$cycloalkyl$C_{1-6}$alkyl or $C_{2-6}$alkenyl, any of which is optionally substituted with Ar, OR⁴, N(R⁴)₂ or CO₂R⁴.

In a third subclass of the compounds of Formula I, m is 0 and n is 1. Within this subclass, X is preferably —C(O)O— or —C(O)N(R⁴)—, and R³ preferably represents $C_{1-6}$alkyl, $C_{3-6}$cycloalkyl, $C_{3-6}$cycloalkyl$C_{1-6}$alkyl or $C_{2-6}$alkenyl, any of which is optionally substituted with Ar, OR⁴, N(R⁴)₂ or CO₂R⁴.

Examples of compounds in accordance with the invention include those in which Ar¹ represents 4-chlorophenyl, Ar² represents 2,5-difluorophenyl, and m, n, R¹, R², R³ and X are as shown in the following table:

| R¹ | m | n | R² | X | R³ |
|---|---|---|---|---|---|
| H | 1 | 1 | —CH(Me)CH₂— | —CO—O— | Me |
| H | 0 | 0 | — | — | —CH(Me)CH₂CH₂OH |
| H | 0 | 0 | — | — | Isopropyl |
| Me | 0 | 0 | — | — | Allyl |
| H | 0 | 0 | — | — | Homoallyl |
| H | 0 | 0 | — | — | 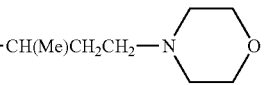 |
| H | 0 | 0 | — | — | Cyclopentyl |
| Me | 0 | 0 | — | — | —CH₂CH₂CH₂OH |
| H | 0 | 0 | — | — | Cyclobutylmethyl |
| H | 1 | 1 | —CH(Me)CH₂— | —CO—NH— | Me |
| H | 0 | 1 | — | —CO—O— | Et |
| Allyl | 0 | 0 | — | — | Allyl |
| H | 1 | 1 | —CH(Me)— | —CO—O— | Et |
| H | 1 | 1 | —CH(Me)CH₂— | —O—CO—NH— | 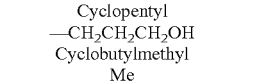 |
| H | 0 | 0 | — | — | —(CH₂)₃CH=CH₂ |
| H | 0 | 0 | — | — | —CH(Me)CH₂OH |
| H | 1 | 1 | —CH₂CH₂— | —CO—O— | Et |
| Allyl | 1 | 1 | —CH₂CH₂— | —CO—O— | Me |
| H | 0 | 0 | — | — | —CH(Me)CH₂CO₂H |
| H | 0 | 0 | — | — | Allyl |
| Allyl | 0 | 0 | — | — | Homoallyl |
| H | 0 | 0 | — | — | 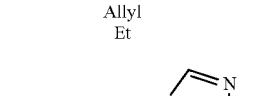 |
| H | 0 | 0 | — | — | 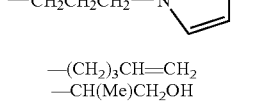 |
| H | 0 | 0 | — | — | Me |
| H | 0 | 0 | — | — | —CH(Me)Ph | and the pharmaceutically acceptable salts thereof.

The compounds of formula I have an activity as modulators of the processing of APP by γ secretase.

The invention also provides pharmaceutical compositions comprising one or more compounds of formula I or pharmaceutically acceptable salts thereof, and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of formula I or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of formula I or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to formula I or a pharmaceutically acceptable salt thereof.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(vinylpyrrolidone) or gelatin.

For treating or preventing Alzheimer's Disease, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

The compounds of formula I may be synthesised by reaction of the benzyl sulphones (1) with a compound of formula (2):

wherein m, n, $R^1$, $R^2$, $R^3$ $Ar^1$ and $Ar^2$ have the same meanings as before, and L represents a leaving group such as halide, especially chloride, bromide or iodide. The reaction is typically carried out in an aprotic solvent such as THF or DMF in the presence of a base such as potassium carbonate, potassium t-butoxide or sodium hydride.

The sulphones (1) where $R^1$ is H are prepared by oxidation of thioethers $Ar^2$—$CH_2$—$SAr^1$ (3), which in turn are formed by reaction of thiols $Ar^1SH$ (4) with benzyl derivatives $Ar^2CH_2$—L (5), where L, $Ar^1$ and $Ar^2$ have the same meanings as before. The reaction between (4) and (5) takes place in an inert solvent such as dichloromethane in the presence of a base such as triethylamine, while the oxidation of (3) to (1) is conveniently effected by m-chloroperoxybenzoic acid, also in an inert solvent such as dichloromethane. The sulphones (1) in which $R^1$ is other than H are prepared by alkylation of $Ar^2CH_2SO_2Ar^1$ with $R^{1a}$—L, where $R^{1a}$ is $R^1$ that is other than H and L, $Ar^1$ and $Ar^2$ have the same meanings as before. The alkylation is conveniently carried out in an aprotic solvent such as THF or DMF in the presence of strong base such as sodium hydride or potassium t-butoxide. Alternatively, alkylation with $R^{1a}$—L may be carried out subsequent to alkylation of sulphones (1) ($R^1$=H) with (2).

An alternative process, suitable for the synthesis of compounds of formula I in which m and n are both 1, X is —CO—O— and $R^2$ is —CH(R)$CH_2$— where R represents H or $C_{1-4}$alkyl, involves base-catalysed addition of a sulphone (1) to an α,β-unsaturated ester (6):

where R and $R^3$ have the same meanings as before. The reaction may be carried out in THF in the presence of potassium t-butoxide at ambient temperature.

A further alternative process, suitable for the synthesis of compounds of formula I in which m is 0, n is 1 and X is —CO—O—, involves nucleophilic displacement of bromine from an α-bromoester $Ar^2$—CHBr—$CO_2R^3$ with $Ar^1$—SH, followed by oxidation of the resulting thioether to the sulphone, and optional alkylation with $R^{1a}$—L, where $Ar^1$, $Ar^2$, $R^{1a}$ and $R^3$ have the same meanings as before. The displacement may be effected in the presence of a base such as triethylamine in dichloromethane at ambient temperature, while the oxidation and optional alkylation may be carried out as described previously.

Individual compounds of formula I prepared by the routes described above may be converted into different compounds in accordance with formula I through the application of known synthetic techniques. For example, esters (7) may be converted to amides (8) by treatment with amines $HN(R^4)R^3$:

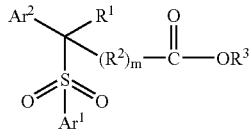
(7)

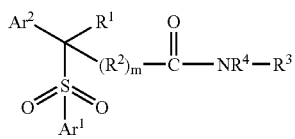
(8)

where $m$, $Ar^1$, $Ar^2$, $R^1$, $R^2$, $R^3$ and $R^4$ have the same meanings as before.

Alternatively, the esters (7) may be hydrolysed to the corresponding carboxylic acids (e.g. by refluxing with LiOH in aqueous THF), which in turn may be coupled with alcohols $R^3OH$ or amines $HN(R^4)R^3$ to provide esters (7) and amides (8) respectively, in which the identity of $R^3$ and/or $R^4$ is varied. Any of the standard coupling techniques may be used, such as conversion of the acid to the acid chloride followed by treatment with the alcohol or amine in the presence of base, or the use of activating agents such as dimethylaminopyridine, hydroxybenzotriazole, dicyclohexylcarbodiimide, carbonyldiimidazole and the like.

The esters (7) may also be reduced to the corresponding primary alcohols (9) (e.g. by treatment with $LiAlH_4$ in THF at 0° C.):

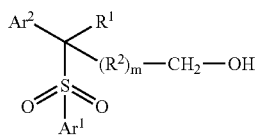
(9)

where $m$, $Ar^1$, $Ar^2$, $R^1$ and $R^2$ have the same meanings as before. Alcohols (9) are effectively compounds of formula I in which $m=n=0$ and $R^3$ is hydroxyalkyl. The hydroxy group may be displaced by a variety of nucleophiles (optionally after conversion to the iodide, mesylate, tosylate or similar), notably by $(R^4)_2NH$. In a typical process, the alcohol (9) is reacted with iodine and triphenylphosphine in the presence of imidazole in a mixture of acetonitrile and ether at 0° C. to form the iodide, which is subsequently treated with the amine $(R^4)_2NH$ in acetonitrile at ambient temperature.

Alternatively, alcohols (9) may be treated with phosgene or 4-nitrophenylchloroformate, and thereafter with alcohols $R^3OH$ or amines $HN(R^4)R^3$ to provide carbonates (10) and carbamates (11) respectively:

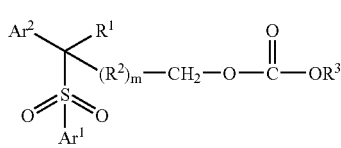
(10)

-continued

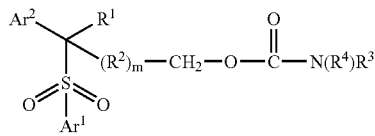
(11)

where $m$, $Ar^1$, $Ar^2$, $R^1$, $R^2$, $R^3$ and $R^4$ have the same meanings as before. The overall effect is thus to extend the $R^2$ group of (7) by one methylene, to replace the ester linkage of (7) by a carbonate or carbamate linkage, and optionally to vary the identitiy of $R^3$.

Where they are not themselves commercially available, the starting materials and reagents employed in the above-described synthetic schemes may be obtained by the application of standard techniques of organic synthesis to commercially available materials.

It will be appreciated that many of the above-described synthetic schemes may give rise to mixtures of stereoisomers. Such mixtures may be separated by conventional means such as fractional crystallisation and preparative chromatography.

Certain compounds according to the invention may exist as optical isomers due to the presence of one or more chiral centres or because of the overall asymmetery of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

A typical assay which can be used to determine the level of activity of compounds of the present invention is as follows:

(1) Mouse neuroblastoma neuro 2a cells expressing human app695 are cultured at 50-70% confluency in the presence of sterile 10mM sodium butyrate.

(2) Cells are placed in 96-well plates at 30,000/well/100 μL in minimal essential medium (EM) (phenol red-free) +10% foetal bovine serum (FBS), 50mM HEPES buffer (pH7.3), 1% glutamine, 0.2mg/ml G418 antibiotic, 10 mM sodium butyrate.

(3) Make dilutions of the compound plate. Dilute stock solution to 5.5% DMSO/110 μM compound. Mix compounds vigorously and store at 40° C. until use.

(4) Add 10 μL compound/well. Mix plate briefly, and leave for 18 h in 37° C. incubator.

(5) Remove 90 μL of culture supernatant and dilute 1:1 with ice-cold 25 mM HEPES (pH.3), 0.1% BSA, 1.0 mM EDTA (+broad spectrum protease inhibitor cocktail; pre-aliquotted into a 96-well plate). Mix and keep on ice or freeze at −80° C.

(6) Add back 100 μL of warm MEM +10% FBS, 50 mM HEPES (pH7.3), 1% glutamine, 0.2 mg/ml G418, 10 mM sodium butyrate to each well, and return plate to 37° C. incubator.

(7) Prepare reagents necessary to determine amyloid peptide levels, for example by ELISA assay.

(8) To determine if compounds are cytotoxic, cell viability following compound administration is assessed by the use of redox dye reduction. A typical example is a combination of redox dye MTS (Promega) and the electron coupling reagent PES. This mixture is made up according to the manufacturer's instructions and left at room temperature.

(9) Quantitate amyloid beta 40 and 42 peptides using an appropriate volume of diluted culture medium by standard ELISA techniques.

(10) Add 15 μL/well MTS/PES solution to the cells; mix and leave at 37° C.

(11) Read plate when the absorbance values are approximately 1.0 (mix briefly before reading to disperse the reduced formazan product).

Alternative assays are described in *Biochemistry*, 2000, 39(30), 8698-8704.

The Examples of the present invention all had an $ED_{50}$ of less than 10 μM, preferably less than 1 μM and most preferably less than 100 μM in at least one of the above assays.

The following examples illustrate the present invention.

EXAMPLES

Intermediate 1

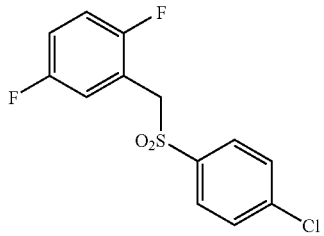

4-Chlorothiophenol (3.6 g, 0.025 mol) in dichloromethane (100 ml) was treated with 2,5-difluorobenzyl bromide (5.17 g, 0.025 mol) and triethylamine (3.9 ml, 0.028 mol), reaction was stirred for 2 hours then diluted with dichloromethane (250 ml) and washed with water (100 ml) and brine (100 ml). The separated organic layer was dried ($MgSO_4$) and evaporated to dryness. Product was purified by passing down a plug of silica eluting with hexane-ethyl acetate mixtures. 5.12 g. $^1$H NMR $CDCl_3$ 7.23 (4H,s), 6.69-6.86 (3H,m) and 4.04 (2H,s).

This thioether (5.12 g, 0.018 mol) was dissolved in dichloromethane (100 ml) and treated with m-chloroperoxybenzoic acid (14.3 g, 0.042 mol (50% w/w)) and stirred for 2 hours. The reaction was then washed with $Na_2S_2O_5$ (5% solution, 100 ml), brine (50 ml), dried ($MgSO_4$) and evaporated to dryness. The sulphone product was purified on silica eluting with hexane-ethyl acetate mixtures, 3.6 g. $^1$H NMR $CDCl_3$ 7.61 (2H,d, J=8.6 Hz), 7.45 (2H,d, J=8.6 Hz), 7.13-7.08 (1H, m), 7.05-7.01 (1H,m), 7.05-7.00 (1H,m), 6.99-6.87 (1H,m) and 4.36 (2h,s).

Example 1

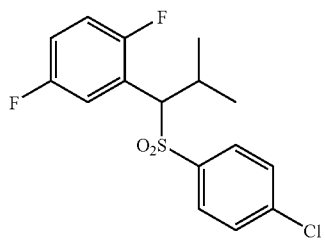

Intermediate 1 (0.2 g, 0.66 mmol) and 2-iodopropane (0.33 ml, 3.3 mmol) in tetrahydrofuran (10 ml) were treated with potassium $^t$butoxide (0.73 ml 1M solution in tetrahydrofuran, 0.72 mmol) and heated at 80° C. for 48 hours. The reaction was then diluted with water and the products extracted into ethyl acetate (100 ml), the organic phase separated, washed with brine (50 ml), dried ($MgSO_4$) and evaporated to dryness. The product was purified on silica eluting with hexane-ethyl acetate mixtures, 0.12 g.

$^1$H NMR $CDCl_3$ 7.52-7.49 (2H,m), 7.45-7.35 (1H,m), 7.32-7.29 (2H,m), 6.94-6.88 (1H,m), 6.77-6.72 (1H,m), 4.32 (1H,d,J=7.1 Hz), 2.86-2.81 (1H,m), 1.31 (3H,d,J=6 Hz) and 0.97 (3H,d,J=6 Hz).

Example 2

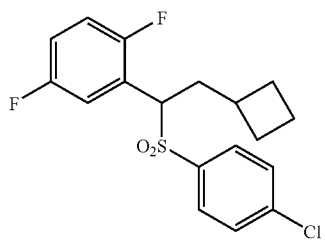

Prepared as described in example 1 using bromomethyl cyclobutane in place of 2-iodopropane. 0.11 g. $^1$H NMR $CDCl_3$ 7.52 (2H,d,J=7.8 Hz), 7.37 (2H,d,J=7.8 Hz), 7.27-7.22 (1H,m), 6.99-6.94 (1H,m), 6.83-6.78 (1H,m), 4.43-4.4 (1H, m), 2.49-2.42 (1H,m), 2.23-2.04 (2H,m), 1.95-1.73 (4H,m) and 1.68-1.55 (2H,m).

Example 3

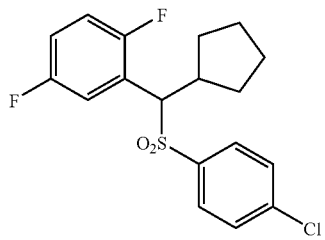

Prepared as described in example 1 using bromocyclopentane in place of 2-iodopropane. 0.15 g. $^1$H NMR $CDCl_3$ 7.51-7.47 (2H,m), 7.33-7.3 (3H,m), 6.93-6.87 (2H,m), 6.75-6.69 (1H,m), 4.42 1H,brd, 10.6 Hz), 2.85-2.75 (1H,m),2.40-2.34 (1H,M), 1.80-1.49 (6H,m) and 1.06-1.0 (1H,m).

Example 4

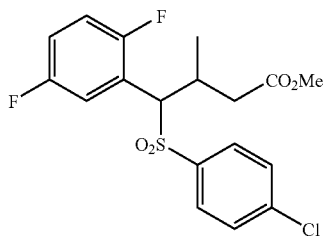

Intermediate 1 (1 g, 3.31 mmol) and methyl crotonate (0.35 ml, 3.31 mmol) in tetrahydrofuran (30 ml) were treated with potassium ᵗbutoxide (3.64 ml 1M solution in tetrahydrofuran, 3.64 mmol) and stirred for 2 hours. The reaction was then partitioned between ethyl acetate (100 ml) and water (100 ml, the organic phase separated, washed with brine (50 ml), dried ($MgSO_4$) and evaporated to dryness. Products were purified on silica eluting with hexane-ethyl acetate mixtures and isolated as a mixture of diastereoisomers. $^1$H NMR $CDCl_3$ 7.55-7.52 (2H,m), 7.51-7.39 (1H,m), 7.35-7.31 (2H,m), 6.97-6.91 (1H,m), 6.81-6.75 (1H,m), 4.84 (1H,d,J=7.8 Hz), 4.62 (1H,d,J=8.2 Hz), 3.71 (3H,s), 3.64 (3H,s), 3.17-3.11 (1H,m), 2.83-2.76 (1H,m), 2.65-2.57 (1H,m), 2.16-2.09 (1H,m), 1,38 (3H,d,J=6.7 Hz) and 1.05 (3H,d,J=6.8 Hz).

Example 5

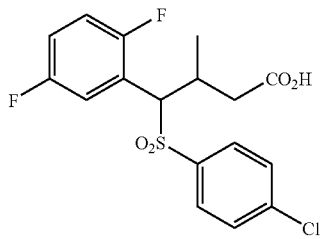

The ester from Example 4, (0.64 g, 1.58 mmol) in tetrahydrofuran (16 ml) was treated with LiOH (0.12 g, 4.75 mmol) in water (4 ml) and heated at 60° C. for 18 hours. The reaction was diluted with ethyl acetate (100 ml) and washed with HCl (1N, 50 ml), brine (50 ml), dried ($MgSO_4$) and evaporated to dryness. Products were purified on silica eluting with hexane-ethyl acetate mixtures and isolated as a mixture of diastereoisomers, 0.52 g. $^1$H NMR $CDCl_3$ 7.58-7.51 2H,m, 7.485-7.4 (1H,m), 7.35-7.32 (2H,m), 6.99-6.94 (1H,m), 6.92-6.75 (1H,m), 4.81 (1H,d,J=8 Hz), 4.63 (1H,d,J=8 Hz), 3.16-3.09 (1H,m), 2.94-2.88 (1H,m), 2.72-2.11 (1H,m), 2.21-2.11 (1H,m), 1.42 (3H,d,J=6.6 Hz) and 1.07 (3H,d,J=6.8 Hz).

Example 6

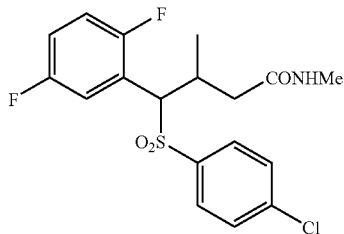

The ester from Example 4, 0.11 g, 0.27 mmol) in methanol was saturated with monomethylamine at 0° C., sealed and stirred for 18 hours. The reaction was then evaporated to dryness and the product purified on silica eluting with hexane-ethyl acetate mixtures and isolated as a mixture of diastereoisomers, 0.06 g. $^1$H NMR $CDCl^3$ 7.55-7.49 (2H,m), 7.42-7.4 (1H,m), 7.36-7.31 (2H,m), 6.95-6.91 (1H,m), 6.81-6.73 (1H,m), 5.74 (1H,br), 5.30 (1H,br), 4.77 (1H,d,J=8.4 Hz), 4.65 (7.6 Hz), 3.15-3.10 (1H,m), 2.84 (3H,d,J=4.8 Hz), 2.77 (3H,d,J=4.8 Hz), 2.7-2.65 (1H,m), 2.57-2.48 (1H,m), 1.96-1.89 (1H,m), 1.34 (3H,d,J=6.7 Hz) and 0.86 (3H,d,J=6.6 Hz).

MS MH+402.

Example 7

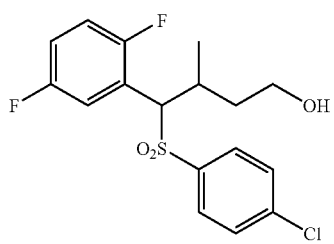

The ester from Example 4 (0.32 g,0.82 mmol) in tetrahydrofuran (20 ml) was cooled to −10° C. and treated with lithium aluminium hydride (1M in tetrahydrofuran, 1.65 ml, 1.65 mmol) and stirred for 2 hours, warming to room temperature. The reaction was quenched with HCl (1N, 50 ml) and diluted with ethyl acetate (100 ml). The organic phase was separated washed with brine (50 ml), dried ($MgSO_4$) and evaporated to dryness. Products were purified on silica eluting with hexane-ethyl acetate mixtures and isolated as a mixture of diastereoisomers, 0.12 g. $^1$H NMR $CDCl_3$ 7.52-7.49 (2H,m), 7.45 (1H,m), 7.33-7.3 (2H,m), 6.95-6.91 (1H,m), 6.78-6.71 (1H,m), 4.67 (1H,d,J=7.3 Hz), 4.50 (1H,d,J=8 Hz), 3.83 (2H,m), 3.05-2.85 (1H,m), 2.05-1.75(2H,m), 1.35 (3H,d,J=8 Hz) and 1.07 (3H,d,J=6.8 Hz).

Example 8

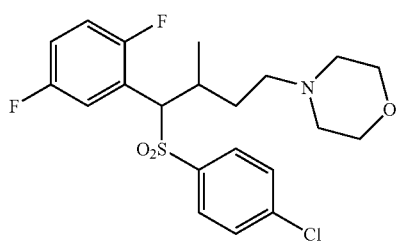

The alcohol from Example 7 (89 mg, 0.24 mmol), triphenylphosphine (63 mg, 0.24 mmol) and imidazole (16 mg, 0.4 mmol) were dissolved in acetonitrile/ether (1:2, 3 ml) cooled to 0° C., treated with iodine (61 mg, 0.24 mmol) and stirred for 12 hours. The solvent was then removed, the residue redissolved in dichloromethane and washed with water (50 ml). The organic phase was separated, washed with brine (50 ml), dried ($MgSO_4$) and evaporated to dryness. Products were purified on silica eluting with hexane-ethyl acetate mixtures and isolated as a mixture of diastereoisomers, 69mg. Diastereoisomer A. $^1$H NMR $CDCl_3$ 7.54 (2H,d,J=8.5 Hz), 7.42

(1H,m), 7.35 (2H,d,J=8.5 Hz), 6.96-6.9 (1H,m), 6.81-6.72 (1H,m), 4.48 (1H,d,J=6.1 Hz), 3.32-3.04 (2H,m), 2.93-2.85 (1H,m), 2.28-2.18 (1H,m), 1.82-1.73 (1H,m) and 1.1 (3H,d, J=6.8 Hz). Diastereoisomer B. 1H NMR CDCl3 7.50 (2H,d, J=8.5 Hz), 7.42 (1H,m), 7.31 (2H,d,J=8.5 Hz), 6.96-6.9 (1H, m), 6.81-6.72 (1H,m), 4.45 (1H,d,J=8.4 Hz), 3.32-3.21 (1H, m), 3.15-3.04 (1H,m), 2.82-2.75 (1H,m), 2.07-2 (1H,m), 1.62-1.53 (1H,m) and 1.35 (3H,d,J=6.6 Hz).

The resulting iodide (69 mg, 0.14 mmol) was dissolved in acetonitrile (3 ml) treated with morpholine ( 13.3 μl, 0.15 mM) and stirred for 30 minutes. The reaction was evaporated to dryness and the products purified on silica eluting with hexane-ethyl acetate mixtures and the product isolated as a mixture of diastereoisomers.

Diastereoisomer A $^1$H NMR CDCl$_3$ 7.53-7.48 (2H, m), 7.48-7.40 (1H, m), 7.34-7.26 (2H, m), 6.94-6.88 (2H, m), 6.77-6.70 (1H, m), 4.46 (1H, d, J=8.2 Hz), 3.70-3.65 (1H, m), 2.90-2.80 (1H, m), 2.51-2.23 (1H, m), 1.80-1.69 (1H, m), 1.32 (3H, d, J=6.6 Hz) and 1.27-1.09 (1H, m). MS MH+444.

Diastereoisomer B. $^1$H NMR CDCl$_3$ 7.54-7.20 (3H, m), 7.34-7.20 (2H, m), 6.97-6.90 (1H, m), 6.81-6.70 (1H, m), 4.57 (1H, d, J=6.4 Hz), 3.72-3.65 (4H, m), 2.91-2.80 (1H, m), 2.48-2.23 (1H, m), 2.04-1.90 (1H, m), 1.27-1.16 (1H, m) and 1.08 (3H, d, J=6.8 Hz). ). MS MH+444.

Example 9

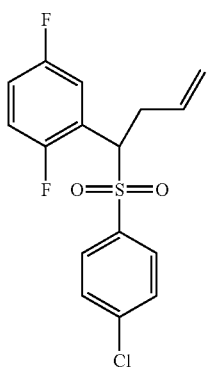

Intermediate 1 (500 mg, 1.66 mmol) in N,N-dimethylformamide (DMF) (2.5 ml) was treated with sodium hydride (73 mg, 60% w/w in mineral oil, 1.82 mmol), then allyl bromide (216 μl, 2.49 mmol). The mixture was stirred at room temperature for 16 hours, a further portion of sodium hydride (36 mg, 60% w/w in mineral oil, 0.91 mmol) added and stirring at room temperature continued for another 5.5 hours. The reaction mixture was diluted with water (40 ml) and extracted with ethyl acetate (3 ×50 ml), and the combined organics washed with brine (sat., 100 ml), dried (Mg SO$_4$) and evaporated to dryness, giving an orange oil (506 mg). This material was chromatographed on silica, eluting with 0-5% ethyl acetate in hexanes to give product 199 mg. $^1$H NMR (400 MHz, CDCl$_3$), 2.79-2.88 (1H, m), 3.17-3.23 (1H, m), 4.57-4.61 (1H, m), 5.00-5.10 (2H, m), 5.50-5.60 (1H, m), 6.79-6.85 (1H, m), 6.94-7.00 (1H, m), 7.23-7.28 (1H, m), 7.38-7.41 (2H, m), 7.53-7.56 (2H, m).

Example 10

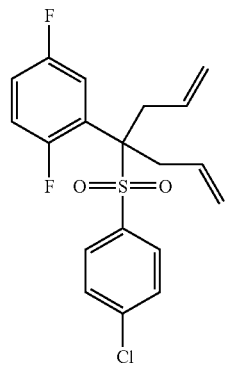

The mono-allyl derivative from Example 9 (50 mg, 0.15 mmol) in tetrahydrofuran (2 ml) was treated with allyl bromide (14 μl, 0.16 mmol). Potassium tert-butoxide (161 μl, 1M solution in tetrahydrofuran, 0.16 mmol) was then dripped in slowly and mixture stirred at room temperature for 2 hours. The reaction mixture was diluted with ethyl acetate (20 ml), washed with water (30 ml) and then brine (sat., 30 ml), then dried (MgSO$_4$) and evaporated to dryness, giving 39 mg crude material. This was purified by preparative t.l.c., eluting with 5% ethyl acetate in hexanes, giving product 10.6 mg. $^1$H NMR (400 MHz, CDCl$_3$), 3.08-3.15 (2H, m), 3.20-3.30 (2H, m), 5.14-5.24 (4H, m), 5.75-5.90 (2H, 6.75-6.82 (1H, m), 6.94-7.00 (2H, m), 7.37 (4H, d, J=8.0 Hz).

Example 11

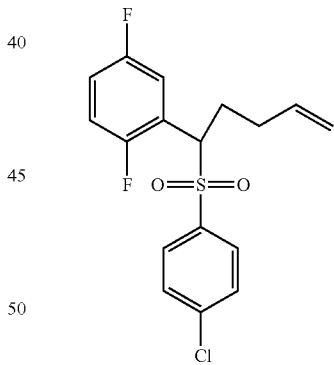

Intermediate 1 (1.01 g, 3.34 mmol) in DMF (3 ml) was dripped into a stirring suspension of sodium hydride (134 mg, 60% w/w in mineral oil, 3.34 mmol) in DMF (2 ml), and the mixture treated with 4-bromo-1-butene (508 μl, 5.01 mmol) and stirred at room temperature for 1.5 hours. The reaction mixture was diluted with water (150 ml) and extracted with ethyl acetate (3×100 ml). The combined organics were washed with brine (sat., 150 ml), dried (MgSO$_4$) and evaporated in vacuo to give 1.05 g crude material which was chromatographed on silica, eluting with 0-5% ethyl acetate in hexanes to give product. 720 mg. $^1$H NMR (360 MHz, CDCl$_3$), 1.85-1.96 (1H, m), 2.06-2.25 (2H, m), 2.49-2.58 (1H, m), 4.54 (1H, dd, J=11.2 Hz and J=2.5 Hz), 4.97 (2H, dq, J=12.9 Hz and J=1.2 Hz), 5.64-5.75 (1H, m), 6.80-6.86 (1H, m), 6.96-7.02 (1H, m), 7.22-7.27 (1H, m), 7.36-7.40 (2H, m), 7.51-7.55 (2H, m).

Example 12

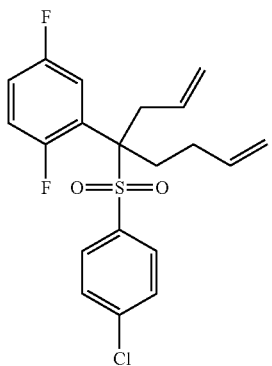

The homoallyl derivative from Example 11 (720 mg, 2.02 mmol) in DMF (10 ml) was dripped into a stirring suspension of sodium hydride (202 mg, 60% w/w in mineral oil, 5.06 mmol) in DMF (7 ml). The mixture was treated with allyl bromide (875 μl, 10.1 mmol) and stirred at room temperature for 64 hours, then diluted with water (150 ml) and extracted with ethyl acetate (3×100 ml). The combined organics were washed with brine (sat., 200 ml), dried (MgSO$_4$) and evaporated in vacuo to give 910 mg crude material which was chromatographed on silica, eluting with 0-5% ethyl acetate in hexanes to give product (794 mg.) A portion of this material (44 mg) was further purified by preparative t.l.c., eluting with 10% ethyl acetate in hexanes to give 36 mg pure product. $^1$H NMR (400 MHz, CDCl$^3$), 1.8-1.95 (1H, m), 2.27-2.33 (1H, m), 2.41-2.46 (2H, m), 3.03 (1H, dd, J=14.8 Hz and J=7.0 Hz), 3.31 (1H, dd, J=15.4 Hz and J=6.3 Hz), 4.99-5.06 (2H, m), 5.18-5.28 (2H, m), 5.73-5.84 (1H, m), 5.90-6.00 (1H m), 6.78-6.86 (1H, m), 7.00-7.08 (2H, m), 7.31-7.37 (4H, m).

Example 13

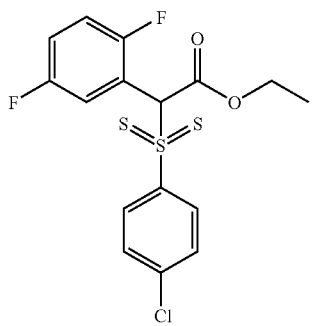

To 2,5-difluorophenylacetic acid (20 g, 116 mmol) in ethanol (400 ml) was added concentrated sulfuric acid (20 ml). The solution was heated at reflux for 18 h and then concentrated. The residue was diluted with ethyl acetate washed with water, saturated aqueous sodium hydrogencarbonate solution, brine, dried (MgSO$_4$), filtered and evaporated to give the ethyl ester.

To the ester (19.5 g, 97 mmol) in carbon tetrachloride (150 ml) and warmed to 40° C. was added N-bromosuccinimide (20.6 g) and then azoisobutyronitrile (100 mg) and the reaction was refluxed for 12 h. After cooling the reaction was diluted with dichloromethane and washed with water and brine. The organic layer was dried (MgSO$_4$), filtered and evaporated. The crude material was purified by flash chromatography (4:1 $^t$hexane/ethyl acetate) to give the α-bromo ester as a light yellow oil (9.5 g).

To 4-chlorothiophenol (1.9 g, 6.9 mmol) in dry dichloromethane (5 ml) at 0° C. under nitrogen were added triethylamine (1.4 ml, 10.3 mmol) and the bromoester (1.9 g, 6.9 mmol) in dry dichloromethane (3 ml). The reaction was allowed to warm to room temperature and stirred for 18 h., diluted with dichloromethane and washed with water and brine. The organic layer was dried (MgSO$_4$), filtered and evaporated. The crude material was purified by flash chromatography (4:1 $^t$hexane/ethyl acetate) to give the thioether as an orange oil (1.25 g) which was dissolved in dichloromethane (10 ml) and treated with m-chloroperoxybenzoic acid in dichloromethane (10 ml). After 3 h the reaction was washed with water, 2M NaOH solution, brine, dried (MgSO$_4$), filtered and evaporated. Purified by flash chromatography (4:1 $^t$hexane/ethyl acetate) to give the title compound (600 mg).

MS (EI+) 375 (MH+)

1H NMR δ(ppm) (CDCl3): 1.29 (3 H, q), 4.23-4.33 (2 H, t), 6.81-6.91 (1 H, s), 6.98-7.04 (2 H, m), 7.28-7.48 (4 H, m).

Example 14

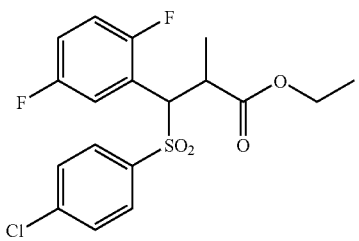

Intermediate 1 (1.37 g, 4.53 mM) and 2-bromopropionic acid ethyl ester (0.85 ml, 9.07 mM) in dimethylformamide (20 ml) were treated with potassium carbonate (1.25 g, 9.07mM) and heated at 80° C. for 18hours. The reaction was then partitioned between ethyl acetate (50 ml) and water (50 ml). The organic phase was separated, washed with brine (50 ml), dried (MgSO$_4$) and evaporated to dryness. Products were purified on silica eluting with hexane-ethyl acetate mixtures and isolated as a mixture of diastereoisomers.

Example 15

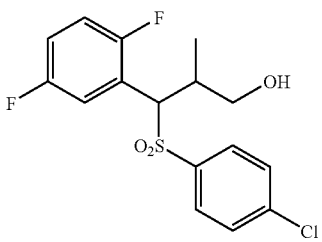

Prepared by reduction of the ester from Example 14 by the procedure of Example 9. MS M+1 361(362).

Example 16

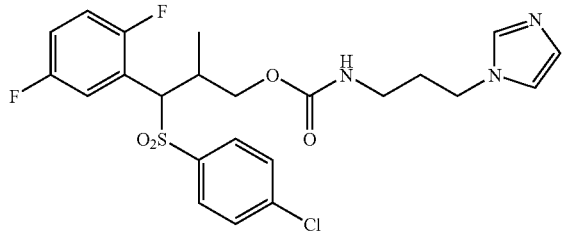

The alcohol from example 15 (0.11 g, 0.31 mM) in acetonitrile (1 ml) and tetrahydrofuran (5 ml) was treated with pyridine (0.026 ml, 0.33 mM) and p-nitrophenylchloroformate. The reaction was stirred for 18 hours before the solvents were evaporated and the residue partitioned between ethyl acetate and brine. The organic phase was separated, washed with brine, dried (MgSO$_4$), and evaporated to dryness. The crude formate was redissolved in acetonitrile/tetrahydrofuran (1:1, 10 ml) and treated with 1-(3-aminopropyl)-imidazole (0.15 ml, 1.24 mM) and stirred at room temperature for 2 hours. The solvents were evaporated and the residue partitioned between ethyl acetate and potassium carbonate (saturated), and the organic phase separated, washed with brine, dried (MgSO$_4$), and evaporated to dryness. The compound was purified on SiO$_2$ eluting with dichloromethane:methanol: ammonia mixtures. $^1$H NMR (360 MHz, CDCl$_3$) 7.54-7.47 (4H, m), 7.34 (2H, d, J=8.5 Hz), 7.05 (1H, s), 6.99-6.94 (2H, m), 6.83-6.77 (1H, m), 4.87 (1H,m) 4.69 (1H, d, J=6.2 Hz), 4.24-4.20 (1H, m), 4.03-3.99 (3H, m), 3.21-3.16 (2H, m), 3.10-3.07 (1H, m), 2.05-1.97 (2H,m), 1.10 (3H, d, J=7 Hz), MS [M+]512 (514).

The invention claimed is:

1. A compound of formula I

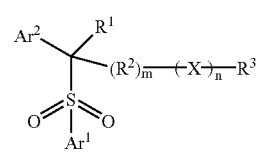

wherein
Ar$^1$ is selected from 4-chlorophenyl, 4-fluorophenyl, 4-trifluoromethylphenyl, 3,4-difluorophenyl, 3,4-dichlorophenyl and 4-methoxyphenyl;
Ar$^2$ is selected from 2,5-dichlorophenyl, 2,5-difluorophenyl and 2-hydroxymethyl-5-fluorophenyl;
R$^1$ represents H, or C$_{1-6}$alkyl or C$_{2-6}$alkenyl, any of which is optionally substituted by halogen, CN, NO$_2$, CF$_3$OH, C$_{1-4}$alkoxy or C$_{1-4}$alkoxycarbonyl;
R$^2$ represents a saturated or unsaturated hydrocarbon linking group of up to 6 carbon atoms;
X represents —O—, —S—, —SO$_2$—, —N(R$^4$)—, —C(O)—, —OC(O)—, —C(O)O—, —C(O)N(R$^4$)—, —N(R$^4$)C(O)—, —OC(O)O—, —N(R$^4$)C(O)O—, —OC(O)N(R$^4$)—, —SO$_2$N(R$^4$)— or —N(R$^4$)SO$_2$—;
R$^3$ represents C$_{1-10}$alkyl, C$_{2-6}$alkenyl or C$_{2-6}$alkynyl, any of which may be substituted by OR$^4$;
R$^4$ represents H or C$_{1-4}$alkyl
m and n are each 0;
or a pharmaceutically acceptable salt thereof.

* * * * *